(12) United States Patent
Hosoya et al.

(10) Patent No.: US 8,470,302 B2
(45) Date of Patent: Jun. 25, 2013

(54) TOOTHPASTE

(75) Inventors: Manabu Hosoya, Tokyo (JP); Kazushi Oshino, Tokyo (JP); Hiromasa Matsumoto, Tokyo (JP); Yoshitaka Kitsunai, Tokyo (JP)

(73) Assignee: Kao Corporation, Tokyo (JP)

( * ) Notice: Subject to any disclaimer, the term of this patent is extended or adjusted under 35 U.S.C. 154(b) by 200 days.

(21) Appl. No.: 12/359,385

(22) Filed: Jan. 26, 2009

(65) Prior Publication Data

US 2009/0136584 A1   May 28, 2009

Related U.S. Application Data

(63) Continuation of application No. 10/492,199, filed as application No. PCT/JP02/11099 on Oct. 25, 2002, now abandoned.

(30) Foreign Application Priority Data

Oct. 25, 2001  (JP) ................................. 2001-327367
Mar. 11, 2002  (JP) ................................. 2002-65550

(51) Int. Cl.
*A61K 8/00*   (2006.01)

(52) U.S. Cl.
USPC .......................................................... 424/49

(58) Field of Classification Search
None
See application file for complete search history.

(56) References Cited

U.S. PATENT DOCUMENTS

| 4,211,341 A | | 7/1980 | Weyn | |
|---|---|---|---|---|
| 4,581,228 A | * | 4/1986 | Suganuma et al. | 424/52 |
| 4,871,396 A | * | 10/1989 | Tsujita et al. | 106/286.8 |
| 4,877,602 A | * | 10/1989 | Uematsu et al. | 424/49 |
| 5,334,375 A | | 8/1994 | Nabi et al. | |
| 5,843,406 A | | 12/1998 | Mordarski et al. | |
| 5,891,473 A | * | 4/1999 | Stanier | 424/489 |
| 5,950,873 A | * | 9/1999 | Williams et al. | 222/137 |
| 5,976,508 A | | 11/1999 | Nabi et al. | |
| 6,039,215 A | * | 3/2000 | Bell | 222/137 |
| 6,358,494 B1 | | 3/2002 | Aoki et al. | |

FOREIGN PATENT DOCUMENTS

| JP | 52-61236 | 5/1977 |
|---|---|---|
| JP | 53-41441 | 4/1978 |
| JP | 58-219107 | 12/1983 |
| JP | 63-112509 | 5/1988 |
| JP | 6-192060 | 7/1994 |
| JP | 6-239721 | 8/1994 |
| JP | 8-175942 | 7/1996 |
| JP | 10-265355 | 10/1998 |
| JP | 2000-191484 | 7/2000 |
| JP | 2001-247439 | 9/2001 |
| JP | 2002-500174 | 1/2002 |
| WO | 99/34769 | 7/1999 |
| WO | 99/47108 | 9/1999 |
| WO | WO 00/62749 | 10/2000 |

OTHER PUBLICATIONS

Barnes, et al. "An Introductionto Rheology" Linear Vioscoelasticity (Chapter 3, (pp. 37-55), 1993.

* cited by examiner

*Primary Examiner* — Brian Gulledge
*Assistant Examiner* — Snigdha Maewall
(74) *Attorney, Agent, or Firm* — Oblon, Spivak, McClelland, Maier & Neustadt, L.L.P.

(57) ABSTRACT

A toothpaste filled in a container which has two chambers and is capable of simultaneously discharging two different compositions filled respectively in the two chambers when the main body of the container is pressed, wherein a ratio of a storage modulus $G_A'$ of Composition (A) filled in one chamber to a storage modulus $G_B'$ of Composition (B) filled in the other chamber falls within a range of from 0.6 to 1.4. By controlling the ratio, it is possible to stably discharge from the container storing these two compositions separately predetermined amounts of these two compositions which will otherwise cause a time-dependent change if they are pre-mixed thereby failing to attain the purpose of their addition.

21 Claims, 1 Drawing Sheet

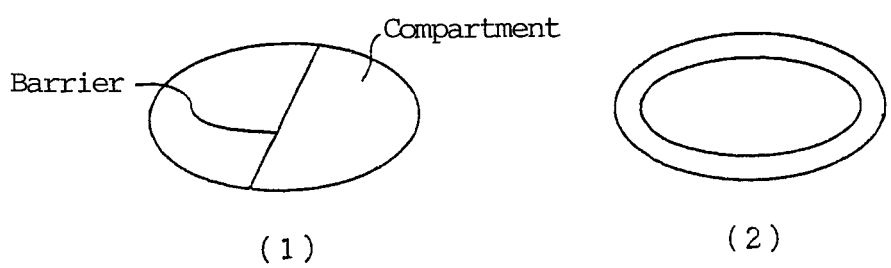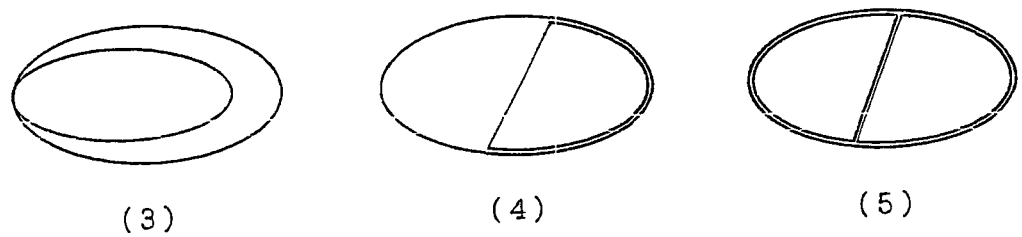

TOOTHPASTE

CROSS REFERENCE TO RELATED APPLICATIONS

This application is a continuation application of U.S. application Ser. No. 10/492,199, filed Apr. 21, 2004, now abandoned which is a national stage of PCT/JP02/11099, filed Oct. 25, 2002, which claims priority from Japanese Patent Application 2001-327367, filed Oct. 25, 2001 and Japanese Patent Application 2002-65550, filed Mar. 11, 2002.

TECHNICAL FIELD

The present invention relates to a toothpaste having two different compositions which are filled separately in two chambers of a container capable of simultaneously discharging therefrom predetermined amounts of these two different compositions.

BACKGROUND ART

The dentin is composed mainly of hydroxyapatite ($Ca_{10}(PO_4)_6(OH)_2$). In the mouth, there is an equilibrium between dissolution (demineralization) of phosphate ions and calcium ions and crystallization (remineralization) of calcium phosphate or hydroxyapatite. At the initial stage of tooth decay, white spots usually appear in the transparent enamel layer of the tooth. If fluoride ions or calcium ions are caused to exist on the tooth surface at this stage, remineralization is promoted by these fluoride ions or calcium ions, resulting in the disappearance of these white spots and recovery of transparency of the enamel layer.

When both fluoride ions and calcium ions are incorporated in one composition in advance, however, they react with each other to form calcium fluoride particles having too large a particle size to be taken readily into the tooth. This results in the problem that a tooth remineralization-promotion effect is not possible.

To overcome this problem, a two-component type oral hygiene product has been proposed (Japanese Patent Application Laid-Open No. Sho 52-61236) in which two components are contained in respective containers and, upon use, they are mixed as needed. The toothpaste disclosed therein is however inconvenient, because the two components filled separately in the respective tubes must be mixed upon use.

Japanese Patent Application Laid-Open No. Sho 53-41441 discloses "a toothpaste composed of at least two components which are mutually reactive and are maintained separately in one dispensing container capable of discharging the content therefrom via a closable orifice". Japanese Patent Application Laid-Open No. Sho 58-219107 discloses a bottle having two compartments as an embodiment physically separating a calcium ion substance and a fluoride ion substance. Japanese Patent Application Laid-Open No. 2001-247439 discloses "a complex toothpaste comprising a first toothpaste component containing tricalcium phosphate as a main effective ingredient; a second toothpaste component containing a fluoride compound as a main effective component; and an integrally-formed container having a plurality of chambers needed to hold these two components separately and a discharge port required for discharging these two components therefrom. In each of the above-described documents, however, no reference is made to discharging of a predetermined amount of each composition filled in the chamber or compartment.

On the other hand, it is difficult to stably discharge the desired amounts of the two compositions filled in the respective chambers or compartments, because they have different components and therefore have different physical properties. In some cases, imbalance in the discharged amount between these two compositions occurs and the amount of one of them is excessively large, while that of the other one is small. It is therefore difficult to stably discharge predetermined amounts of these two compositions every time they are discharged. In particular, when one of the compositions contains granules and the other one does not, the above-described problem is pronounced owing to a difference in the physical properties attributable to the presence or absence of the granules, making it difficult to simultaneously and stably discharge desired amounts of these two compositions whenever they are discharged.

The present invention relates to a toothpaste containing two compositions prepared separately in advance as respective compositions and filled separately in a tube container capable of discharging a mixture of the compositions each in a predetermined amount, said two compositions, when mixed in advance, being not able to achieve the intended object of the invention.

DISCLOSURE OF THE INVENTION

The present inventors have carried out an investigation on a composition, paying attention to the viscoelastic behavior of the composition. As a result, it has been found that squeezed amounts of two different compositions which have been filled in the respective chambers of a tube container can be controlled by specifying a ratio of the storage modulus G'A of one composition (A) filled in one chamber to the storage modulus $G'_B$ of the other composition (B) filled in the other chamber, particularly a ratio of the storage modulus ($G'_A/G'_B$) at tan δ=1, leading to the completion of the present invention.

In the present invention, there is thus provided a toothpaste having two compositions filled separately in two chambers of a container capable of simultaneously discharging therefrom these two compositions when the body of the container is pressed, wherein a ratio of the storage modulus $G_A'$ of one composition (A) in one chamber to the storage modulus G'B of the other composition (B) in another chamber falls within a range of from 0.6 to 1.4, preferably a ratio $G_A'/G_B'$ of the storage modulus at tan δ=1 falls within a range of from 0.6/1 to 1/0.6.

BRIEF DESCRIPTION OF THE DRAWING

FIG. 1 illustrates transverse cross-sections (5 type) of toothpaste containers.

IN A PREFERRED EMBODIMENT

In the present invention, the storage modulus G' is a value (Pa) as measured by a rheometer ("MCR300", product of Paar Physica) when 0.1 to 1000% strain is applied under the following conditions: use of a 25 mm Parallel Plate, plate-plate distance of 0.7 mm, frequency of 0.16 Hz, and measuring temperature of 25° C. The measuring method is not limited thereto, wherein a rheometer is preferred, and various commercially available ones are usable.

The initial modulus $G_0'$ is determined by the following measuring method. The composition is placed on the testing stand of a rheometer and clamped with parallel plates to give a predetermined thickness. After it is allowed to stand for 15 minutes to sufficiently relax the stress applied to the sample upon clamping, measurement is started. The storage modulus G' and loss modulus G" are measured while changing the intensity of the strain in 20 steps from 0.1% to 1000% strain at an equal interval on a common logarithm. The initial modulus $G_0'$ is the value at the third step in 20 steps, that is, a storage modulus G' when 0.25% strain is applied.

The initial modulus $G_0'$, storage modulus G' and storage modulus G' at tan δ=δ1 can be adjusted to desired values by controlling the content of each component in the composition. For example, a composition having desired initial modulus $G_0'$ and modulus G' at tan δ=1 can be obtained as shown below in Table 1 by using two kinds of silicas different in an oil absorption amount and two kinds of sodium carboxymethylcelluloses different in degree of etherification.

The term "tan δ" as used herein means a ratio of the storage modulus G' to the loss modulus G" (tan δ=G"/G'). The storage modulus G' and loss modulus G" are parameters indicating the dynamic viscoelasticity, details of which are described specifically, for example, in "Oishisa no Rheology", Nobuko Nakahama, Hiro Ogoshi, Hatsue Moritaka (Kougaku Shuppan), p 22-26".

The two kinds of silicas different in an oil absorption amount and used for the adjustment of the modulus G' are, for example, two kinds of silicas selected from those having an oil absorption amount ranging from 50 to 400 mL/100 g. Examples of the commercially available silicas different in an oil absorption amount include "SORBOSIL" (product of CROSFIELD) and "SYLOPURE" (product of Fuji Silysia Chemical Ltd).

The oil absorption amount can be measured by a method in accordance with JIS K5101.

As the two kinds of sodium carboxymethylcelluloses different in degree of etherification, two kinds of carboxymethylcelluloses selected from carboxymethylcelluloses having a degree of etherification ranging from 0.3 to 2.0 can be used. Specific examples of the carboxymethylcelluloses different in degree of etherification include "CMC Daicels" produced by Daicel Chemical Industries.

The initial modulus $G_0'$ and the modulus G' at tan δ=1 are adjusted by properly using them in combination. Specifically, for example, the initial modulus $G_0'$ and the modulus G' at tan δ=1 both increase by increasing the incorporation ratio of a silica having a larger oil absorption amount as shown later in Table 2. The initial modulus $G_0'$ increases and the modulus G' at tan δ=1 lowers by increasing the incorporation ratio of a carboxymethylcellulose having a lower degree of etherification.

In the present invention, a ratio $G_A'/G_B'$ of the modulus of Composition (A) to that of Composition (B), in which both of the compositions are filled in the respective chambers of the container, is from 0.6 to 1.4, preferably from 0.8 to 1.25, more preferably from 0.9 to 1.11, especially preferably 1 ($G_A'/G_B'=1$).

In order to constantly discharge the two compositions in equal amounts, it is preferred to adjust the ratio of $G'_A/G'_B$ at tan δ=1 to fall within a range of from 0.6/1 to 1/0.6, preferably from 0.8/1 to 1/0.8, more preferably from 0.9/1 to 1/0.9, especially preferably 1. In addition, it is preferred to adjust the initial storage modulus G' of each of the two compositions to fall within a range of from 200 to 2000 Pa.

In the two compositions of the toothpaste of the present invention, that is, Composition (A) and Composition (B), two components which will react with each other and undergo a time-dependent change to fail to attain the purpose of the invention are incorporated separately. For example, a calcium ion-supplying compound is incorporated into Composition (A), while a fluoride ion-supplying compound is incorporated into Composition (B). Since these compounds are filled in separate chambers of a container, they do not react with each other. When the container is pressed, they are discharged simultaneously from separate chambers, react with each other in an oral cavity, and form fine particles of calcium fluoride in the vicinity of the tooth surface, thereby bringing about excellent remineralization promoting effects of the tooth.

Examples of the calcium ion-supplying compound contained in Composition (A) include calcium lactate, calcium carbonate, calcium secondary phosphate, calcium tertiary phosphate, calcium pyrophosphate, and calcium sulfate. In Composition (A), not only the calcium ion-supplying compound, but also a powdery component such as water insoluble sodium metaphosphate, silica, aluminum hydroxide, magnesium phosphate, zeolite, aluminosilicate composite, magnesium carbonate or red iron oxide may be incorporated.

When the powdery component is added, the average particle size of its primary particles is 0.1 to 10 μm, preferably from 0.3 to 7 μm, more preferably from 0.5 to 2 μm. The term "average particle size" as used herein means a value as measured by a laser diffraction/scattering particle size distribution analyzer.

The calcium ion-supplying compound is preferably incorporated in Composition (A) in an amount of from 50 to 16000 ppm, more preferably from 200 to 8000 ppm, even more preferably from 800 to 8000 ppm, each in terms of calcium ion.

Composition A preferably contains granules and their average particle size is preferably from 50 to 500 μm. The term "average particle size" as used herein means a value as measured by a laser diffraction/scattering particle size distribution analyzer, and from the viewpoint of the feeling during teeth brushing, the particle size from 90 to 400 μm is especially preferred.

For these granules, water can be used as a binder, and either an organic or inorganic binder can also be used. Examples of the organic binder include water soluble polymers such as polyacrylic acid, polyvinyl alcohol and polyethylene glycol, polysaccharides such as hydroxyethylcellulose, carboxymethylcellulose, hydroxypropylcellulose, xanthan gum and carrageenan, water insoluble polymers such as natural fibers, polyvinyl chloride, polyethylene, polypropylene, polystyrene, poly(methyl methacrylate), nylon and silicone, and oils or fats such as paraffin, higher alcohols and waxes. Examples of the inorganic binders include water soluble metal salts such as sodium chloride and potassium chloride, water soluble metal salts of an organic acid such as sodium citrate, sodium tartrate and sodium siccinate, and non-water-soluble compounds such as colloidal silica, magnesium aluminometasilicate, bentonite, montmorillonite, kaolin, synthetic aluminum silicate, celcium silicate, aluminum hydroxide gel, alumina sol, magnesium carbonate, synthetic hydrotalcite, magnesium oxide and magnesium hydroxide. These binders may be used in combination of at least two of them. From the viewpoint of the stability of granules in the toothpaste, the inorganic non-water-soluble compounds are preferred as the binder, with colloidal silica and synthetic aluminum silicate being particularly preferred.

As the granules, those disintegrated under a load of from 0.1 to 50 g, preferably from 3 to 15 g per granule are preferred, because they are excellent in plaque removing performance, and at such disintegration strength, they are disintegrated moderately by brushing without inducing a foreign-matter sensation in the oral cavity.

Such granules are prepared by spray granulation, spray cooling, extrusion, pressing, cutting or granulation method.

The toothpaste of the present invention preferably contains 1 to 50 mass %, more preferably from 3 to 40 mass %, even more preferably from 5 to 30 mass % of granules in the whole toothpaste.

As the fluoride ion-supplying compound contained in Composition (B), either an inorganic compound or an organic compound may be used. Specific examples include sodium fluoride, potassium fluoride, tin fluoride, sodium fluosilicate, sodium monofluorophosphate, aluminum fluoride, silver fluoride, hexylamine hydrofluoride, decanolamine hydrofluoride, and octadecenylamine hydrofluoride. Of these, use of sodium monofluorophosphate or sodium fluoride is especially preferred. The content of the fluoride ion-supplying compound in the total amount of the toothpaste of the present invention is preferably from 0.002 to 1 mass %, especially from 0.01 to 0.2 mass %, in terms of fluorine.

Compositions (A) and (B) of the toothpaste of the present invention may contain, in addition to the above-described components, a humectant such as glycerin and polyethylene glycol, an effervescent agent, a bond such as sodium carboxymethyl cellulose, carrageenan and silica, a sweetener such as sodium saccharin, a colorant, a preservative such as methyl paraoxybenzoate, a bactericide such as benzethonium chloride, isopropylmethylphenol and triclosan, an anti-inflammatory agent, and a flavor.

The toothpaste of the present invention can be prepared by adjusting the contents of the above-described components, and filling Composition (A) and Composition (B), which have been adjusted to have a ratio of the modulus $G'_A/G'_B$ within a predetermined range, in respective chambers of a container capable of discharging the content when a pressure is applied.

As the container, various containers capable of discharging the content filled therein when the body of the container is pressed can be used. It is preferable to use a container which has been obtained by stacking thin metal films or thin plastic films to form a tube, sealing one end of the tube, and providing, a discharge port for simultaneously discharging plural contents at the other end of the tube and, inside of the tube, a plurality of compartments each connected with the discharge port and extending from the one end of the tube to the other end of the tube. With such a structure, it is possible to apply equal pressure to these compartments whenever pressure is applied.

The compartments include those obtained by disposing a barrier inside of the container to prevent mixing of the two compositions, bag-like compartments, those obtained by inserting smaller container(s) in the main container, and those obtained by joining containers at the discharge port. Any of these compartments has one end connected with the discharge port of the container. In addition, it is preferred that a ratio of the cross-sectional areas of the two compartments ($R_C$) and a ratio of the volumes of the two compartments ($R_V$) are approximately equal, specifically, $R_C/R_V$ is within a range of from) 0.9/1 to 1/0.9.

FIG. 1 illustrates examples of the cross-sections of the containers having compartments therein. They are: a container divided into two compartments disposed inside thereof (FIG. 1(1)), that having two cylindrical compartments disposed concentrically (FIG. 1(2)), that having two cylindrical compartments disposed eccentrically (FIG. 1(3)), that having one semi-columnar compartment disposed therein (FIG. 1(4)), and that having two semi-columnar compartments disposed therein (FIG. 1(5)).

EXAMPLES

Examples 1 and 2

Compositions of A group and B group shown in Tables 1 and 2 were prepared. Composition A and Composition B were filled respectively in two 60-mL compartments of a toothpaste container having the cross-section shown in FIG. 1(5).

Test on Discharge Property:

The bottom (sealed portion) of the container was inserted lightly into a tube compressor having two rubber rolls which had a diameter of 5 cm and were arranged with a clearance of 0.5 mm, and stress was applied to the tube by rotating the rolls. The container was pressed so that the toothpaste 1 cm in length was squeezed out and the mass of each of Composition A and Composition B was measured. The mass ratio of Composition B ($W_B$) to Composition A ($W_A$) was calculated.

Judgment on discharge property:

©: $1/1.1 \geq W_B/W_A \leq 1.1$

X: $W_B/W_A < 0.6$ or $W_B/W_A > 1/0.6$

TABLE 1

|  | (parts by mass) | |
| --- | --- | --- |
|  | Composition A-1 | Composition A-2 |
| Carboxymethylcellulose (degree of etherification: 1.0 to 1.5) | 1.2 | 0.7 |
| Carboxymethylcellulose (degree of etherification: 0.6 to 0.8) | 0.2 | 0.4 |
| Silica (oil absorption amount: 260 mL/100 g) | 6.0 | 6.0 |
| Silica (oil absorption amount: 130 mL/100 g) | — | 14.0 |
| Calcium carbonate (average particle size: 150 μm) | 14.0 | — |
| Sodium monofluorophosphate | 0.73 | 0.73 |
| Sorbitol solution | 40.83 | 40.83 |
| Polyethylene glycol 600 | 4.0 | 4.0 |
| Sodium saccharin | 0.14 | 0.14 |
| Sodium lauryl sulfate | 1.2 | 1.2 |
| Flavor | 1.0 | 1.0 |
| Blue No. 1 (0.6%) | 0.1 | 0.1 |
| Purified water | Balance | Balance |
| Initial modulus G' [Pa] | 427 | 1600 |
| Modulus G' at tan δ = 1 [Pa] | 226 | 177 |

TABLE 2

|  | Composition B-1 | Composition B-2 | Composition B-3 | Composition B-4 | Composition B-5 | Composition B-6 |
|---|---|---|---|---|---|---|
| | | | | | | (parts by mass) |
| Carboxymethylcellulose (degree of etherification: 1.0 to 1.5) | 1.1 | 1.1 | 1.1 | 1.1 | 1.1 | 0.9 |
| Carboxymethylcellulose (degree of etherification: 0.6 to 0.8) | 0 | 0 | 0 | 0 | 0 | 0.2 |
| Silica (oil absorption amount: 260 mL/100 g) | 8.0 | 7.0 | 6.0 | 5.0 | 4.0 | 5.0 |
| Silica (oil absorption amount: 130 mL/100 g) | 11.0 | 13.0 | 13.0 | 14.0 | 15.0 | 14.0 |
| Sodium fluoride | 0.2 | 0.2 | 0.2 | 0.2 | 0.2 | 0.2 |
| Sorbitol solution | 38.5 | 38.5 | 38.5 | 38.5 | 38.5 | 38.5 |
| Polyethylene glycol 600 | 4.0 | 4.0 | 4.0 | 4.0 | 4.0 | 4.0 |
| Sodium saccharin | 0.1 | 0.1 | 0.1 | 0.1 | 0.1 | 0.1 |
| Sodium lauryl sulfate | 1.2 | 1.2 | 1.2 | 1.2 | 1.2 | 1.2 |
| Flavor | 1.0 | 1.0 | 1.0 | 1.0 | 1.0 | 1.0 |
| Purified water | Balance | Balance | Balance | Balance | Balance | Balance |
| Initial modulus G' [Pa] | 2500 | 1700 | 946 | 564 | 147 | 776 |
| Modulus G' at tan δ = 1 [Pa] | 425 | 322 | 239 | 174 | 123 | 144 |

As is apparent from Table 3, ratios of the modulus, $G_A'/G_B'$, at tan δ=1 were 0.95 and 1.02, respectively, in Examples 1 and 2, suggesting that the toothpastes have a good discharge property. In each example, by controlling the ratio $G_A'/G_B'$ of the storage modulus of the compositions to fall within a range of from 0.6/1 to 1/0.6, predetermined amounts of compositions were discharged stably whenever the toothpaste was squeezed.

On the other hand, in the toothpastes in Comparative Examples 1 and 2, the ratios $G_A'/G_B'$ of the storage modulus at tan δ=1 were 0.53 and 0.55, respectively, and the toothpastes had an inferior discharge property. Two-component type toothpastes put on the American market were also tested for their discharge property. The results are shown in Table 3. The ratios $G_A'/G_B'$ of the storage modulus of these pastes at tan δ=1 were booth 0.46 and they were inferior in their discharge property. In the toothpastes of Comparative Examples or commercially available ones, two compositions differ greatly in G' and thus the discharged amount of one of the compositions is excessively larger or excessively smaller, resulting in a failure to stably discharge predetermined amounts of the compositions each time they are used.

Examples 3 and 4

Compositions A and B shown in Table 4 were prepared and they were filled respectively in two 60-mL compartments of a toothpaste container having the cross-section as shown in FIG. 1(5).

The discharge property was evaluated as in Examples 1 and 2. As a result, as apparent from Table 4, although each of the Compositions (B) of Examples 3 and 4 and Comparative Examples 3 and 4 has a viscosity of 3000 dPa·S (25° C.), the ratios $G_A'/G_B'$'s of the toothpastes of Examples 3 and 4 are 0.91 and 0.73, respectively, and these toothpastes have good discharge properties. The ratios $G_A'/G_B'$'s of the toothpastes of Comparative Examples 3 and 4 are, on the other hand, 1.45 and 1.8, respectively, and these toothpastes have inferior discharge properties. It is not always possible to discharge predetermined amounts of the compositions stably by controlling the viscosity of the compositions, but by adjusting the ratio $G_A'/G_B'$ of the storage modulus within a range of from 0.6 to 1.4, predetermined amounts of the compositions can be discharged stably.

TABLE 3

|  |  | Ex. 1 | Ex. 2 | Comp. Ex. 1 | Comp. Ex. 2 | P&G Crest | Colgate Sensitive |
|---|---|---|---|---|---|---|---|
| Compositions | Group A | A-1 | A-2 | A-1 | A-2 | Blue paste | Blue paste |
| | Group B | B-3 | B-4 | B-1 | B-2 | White paste | White paste |
| Initial modulus G' [Pa] | Group A | 427 | 1600 | 427 | 1600 | 540 | 375 |
| | Group B | 946 | 564 | 2500 | 1700 | 1020 | 807 |
| Modulus G' at tan δ = 1 [Pa] | Group A | 226 | 177 | 226 | 177 | 97 | 85 |
| | Group B | 239 | 174 | 425 | 322 | 211 | 186 |
| Ratio of modulus G' at tan δ = 1 ($G_A'/G_B'$) | | 0.95 | 1.02 | 0.53 | 0.55 | 0.46 | 0.46 |
| Discharge property | | ◎ | ◎ | X | X | X | X |

The toothpastes of Examples 3 and 4 did not undergo any change in its discharge property and in components even if they were discharged after storing at 25° C. for 3 months.

TABLE 4

(parts by mass)

|  | Example 3 | | Example 4 | | Comp. Ex. 3 | | Comp. Ex. 4 | |
| --- | --- | --- | --- | --- | --- | --- | --- | --- |
|  | A | B | A | B | A | B | A | B |
| Calcium carbonate (average particle size: 150 μm) | 25 | — | 15 | — | 35 | — | 40 | — |
| Sodium pyrophosphate | 2 | — | 2 | — | 2 | — | 2 | — |
| Sodium monofluorophosphate | 0.73 | — | 0.73 | — | 0.73 | — | 0.73 | — |
| Sodium fluoride | — | 0.2 | — | 0.2 | — | 0.2 | — | 0.2 |
| Sorbitol solution (a 70 wt. % solution) | 36 | 40 | 36 | 40 | 36 | 40 | 36 | 40 |
| Polyethylene glycol 600 | 4 | 4 | 4 | 4 | 4 | 4 | 4 | 4 |
| Sodium saccharin | 0.13 | 0.13 | 0.13 | 0.13 | 0.13 | 0.13 | 0.13 | 0.13 |
| Sodium lauryl sulfate | 1.3 | 1.3 | 1.3 | 1.3 | 1.3 | 1.3 | 1.3 | 1.3 |
| Silicic acid anhydride | 7 | 15 | 7 | 15 | 7 | 15 | 7 | 15 |
| Sodium carboxymethylcellulose | 1 | 1 | 1 | 1 | 1 | 1 | 1 | 1 |
| Flavor | 1 | 1 | 1 | 1 | 1 | 1 | 1 | 1 |
| Purified water | Balance | Balance | Balance | Balance | Balance | Balance | Balance | Balance |
| Total | 100 | 100 | 100 | 100 | 100 | 100 | 100 | 100 |
| Viscosity of composition (dPa·s) 25° C. | 4000 | 3000 | 3000 | 3000 | 5000 | 3000 | 5500 | 3000 |
| Storage modulus (G') | 1000 | 1100 | 800 | 1100 | 1600 | 1100 | 2000 | 1100 |
| Ratio of storage modulus of two compositions ($G_A'/G_B'$) | 0.91 | | 0.73 | | 1.45 | | 1.8 | |
| Discharge property | ⊚ | | ⊚ | | X | | X | |

INDUSTRIAL APPLICABILITY

In the toothpaste of the present invention containing Composition A and Composition B filled separately in a container having two separate chambers, it is possible to discharge the compositions in predetermined amounts from the container by controlling the ratio of the storage modulus $G_A'$ of Composition (A) to the storage modulus $G_B'$ of Composition (B), wherein said Composition A and Composition B are such compositions which, if pre-mixed, will otherwise cause time-dependent change and fail to achieve the intended purpose of the invention.

The invention claimed is:

1. A method for producing a toothpaste container comprising two different toothpaste compositions, wherein each of the compositions has a different physical property depending on a difference of compositional ingredients contained in the compositions, the method comprising:
   filling separately in two chambers of the container capable of simultaneously discharging therefrom the two compositions when the body of the container is pressed, wherein at least one of the two compositions comprises at least two carboxymethylcellulose having different etherificaiton degrees and at least one silica, wherein the at least one silica is selected from the group consisting of at least two different silica having different oil absorption amounts and a mixtures thereof, and wherein a ratio of a storage modulus $G_A'$ measured by a rheometer of one composition (A) in one chamber to a storage modulus $G_B'$ measured by a rheometer of the other composition (B) in another chamber falls within a range of from 0.8/1 to 1/0.8 at tan δ=1, wherein the ratio is obtained by combining said at least two carboxymethylcelluloses having different etherificaiton degrees, said at least two silica having different oil absorption amounts, or by controlling the oil absorption amount of said silica and the etherificaiton degree of said carboxymethylcelluloses in combination,
   wherein the degrees of etherificaiton are in a range of from 0.6 to 1.5, and
   wherein the oil absorption is in a range of from 130 to 400 ml/100 g.

2. The method of claim 1, further comprising:
   stacking thin metal films or thin plastic films to form a tube, sealing one end of the tube, and
   providing a discharge port for simultaneously discharging a plurality of compositions at the other end of the tube, wherein the inside of the tube comprises a plurality of compartments each connected with the discharge port and extending from the one end of the tube to the other end of the tube.

3. The method of claim 1, wherein the composition (A) comprises a calcium ion-supplying compound, while the composition (B) comprises a fluoride ion-supplying compound.

4. The toothpaste container of claim 1, wherein the composition (A) comprises granules.

5. The method of claim 4, wherein the average particle size of the granules is from 50 to 500 μm.

6. The method of claim 4, wherein the granules disintegrate under a load of from 0.1 to 50 g.

7. The method of claim 4, wherein an amount of the granules is from 1 to 50 mass %, based on the entire toothpaste compositions.

8. The method of claim 3, wherein the calcium ion-supplying compound is at least one selected from the group consisting of calcium lactate, calcium carbonate, calcium secondary phosphate, calcium tertiary phosphate, calcium pyrophosphate, and calcium sulfate.

9. The method of claim 3, wherein an amount of the calcium ion-supplying compound is from 50 to 16000 ppm.

10. The method of claim 1, wherein the composition (A) further comprises a powdery component selected from the group consisting of insoluble sodium metaphosphate, silica, aluminum hydroxide, magnesium phosphate, zeolite, aluminosilicate composite, magnesium carbonate, and red iron oxide.

11. The method of claim 10, wherein an average particle size of primary particles of the powdery component is from 0.1 to 10 μm.

12. The method of claim 3, wherein the fluoride ion-supplying compound is at least one selected from the group consisting of sodium fluoride, potassium fluoride, tin fluoride, sodium fluosilicate, sodium monofluorophosphate, aluminum fluoride, silver fluoride, hexylamine hydrofluoride, decanolamine hydrofluoride, and octadecenylamine hydrofluoride.

13. The method of claim 3, wherein an amount of the fluoride ion-supplying compound is from 0.002 to 1 mass % in terms of fluorine.

14. The method of claim 1, wherein a ratio of cross-sectional areas of the two chambers ($R_c$) and a ratio of volumes of the two compartments ($R_v$) is approximately equal, and $R_c/R_v$ is from 0.9/1 to 1/0.9.

15. The method of claim 1, wherein two different ingredients, which can change over time when co-existing with each other, are separately filled in the compositions (A) and the composition (B).

16. The method of claim 1, wherein an initial modulus G' of each of the two different compositions is from 200 to 2,000 Pa when 0.25% strain is applied by a rheometer.

17. A method for producing a toothpaste container comprising two different toothpaste compositions, wherein each of the compositions has a different physical property depending on a difference of compositional ingredients contained in the compositions, the method comprising:
   filling separately in two chambers of the container capable of simultaneously discharging therefrom the two compositions when the body of the container is pressed,
   wherein at least one of the two compositions comprises at least two carboxymethylcellulose having different etherificaiton degrees and at least one silica, wherein the at least one silica is selected from the group consisting of at least two different silica having different oil absorption amounts and a mixtures thereof,
   wherein a ratio of a storage modulus $G_A'$ measured by a rheometer of one composition (A) in one chamber to a storage modulus $G_B'$ measured by a rheometer of the other composition (B) in another chamber falls within a range of from 0.8/1 to 1/0.8 at tan δ=1, wherein the ratio is obtained by combining said at least two carboxymethylcelluloses having different etherificaiton degrees, said at least two silica having different oil absorption amounts, or by controlling the oil absorption amount of said silica and the etherificaiton degree of said carboxymethylcelluloses in combination, and
   wherein the at least two different types of carboxymethylcellulose having different etherificaiton degrees are at least two different types of sodium carboxymethylcellulose having different etherificaiton degrees, and
   wherein the degrees of etherificaiton are in a range of from 0.6 to 1.5, and
   wherein the oil absorption is in a range of from 130 to 400 ml/100 g.

18. The method of claim 17, wherein one of the at least two different types of sodium carboxymethylcellulose having different etherificaiton degrees has etherificaiton degree of 0.6 to 0.8 and one of the at least two different types of sodium carboxymethylcellulose has etherificaiton degree of 1.0 to 1.5.

19. A method for producing a toothpaste container comprising two different toothpaste compositions, wherein each of the compositions has a different physical property depending on a difference of compositional ingredients contained in the compositions, the method comprising:
   filling separately in two chambers of the container capable of simultaneously discharging therefrom the two compositions when the body of the container is pressed,
   wherein one of the two compositions comprises two carboxymethylcellulose having different etherificaiton degrees and one silica or two silica having different oil absorption amounts, and
   wherein the other of the two compositions comprises two silica having different oil absorption amounts and one carboxymethylcellulose or two carboxymethylcellulose having different etherificaiton degrees, and
   wherein a ratio of a storage modulus $G_A'$ measured by a rheometer of one composition (A) in one chamber to a storage modulus $G_B'$ measured by a rheometer of the other composition (B) in another chamber falls within a range of from 0.8/1 to 1/0.8 at tan δ=1, wherein the ratio is obtained by combining said two carboxymethylcelluloses having different etherificaiton degrees, said two silica having different oil absorption amounts, or by controlling the oil absorption amount of said silica and the etherificaiton degree of said carboxymethylcelluloses in combination,
   wherein the degrees of etherificaiton are in a range of from 0.6 to 1.5, and
   wherein the oil absorption is in a range of from 130 to 400 ml/100 g.

20. The method of claim 19, wherein one of the at least two different types of sodium carboxymethylcellulose having different etherificaiton degrees has etherificaiton degree of 0.6 to 0.8 and one of the at least two different types of sodium carboxymethylcellulose has etherificaiton degree of 1.0 to 1.5.

21. The method of claim 20, wherein the ratio of a storage modulus $G_A'$ to a storage modulus $G_B'$ is from 0.9/1 to 1/0.9.

* * * * *